United States Patent [19]

Lenihan, Jr. et al.

[11] 4,309,286
[45] Jan. 5, 1982

[54] LOWER SEALING MEANS FOR CHROMATOGRAPHIC COLUMN

[76] Inventors: Harry J. Lenihan, Jr., 2356 Kuhlview Dr., Pittsburgh, Pa. 15237; Thomas C. Evans, Jr., Wingdate Dr., Wexford, Pa. 15090

[21] Appl. No.: 151,738

[22] Filed: May 20, 1980

[51] Int. Cl.³ ............................................. G01N 31/08
[52] U.S. Cl. ............................... 210/198.2; 73/61.1 C
[58] Field of Search ............ 422/70; 210/198.2, 198.3, 210/656, 659, 238, 289, 474, 476, 477; 73/61.1 C; 55/386

[56] References Cited

U.S. PATENT DOCUMENTS

| | | | |
|---|---|---|---|
| 3,539,300 | 11/1970 | Stone | 23/230 B X |
| 3,682,321 | 7/1972 | Smith | 210/477 |
| 3,815,752 | 6/1974 | Hoffman et al. | 210/289 X |
| 4,155,846 | 5/1979 | Novak et al. | 210/659 |
| 4,162,979 | 7/1979 | Wahlefeld et al. | 210/477 X |
| 4,168,147 | 9/1979 | Acuff | 422/70 X |

*Primary Examiner*—Arnold Turk
*Attorney, Agent, or Firm*—Robert D. Yeager

[57] ABSTRACT

An improved lower sealing means for a chromatographic column including a disc of phase separation paper transversely disposed within the column at its bottom portion and a flanged retaining ring in contact with the paper disc at its periphery and sealingly engaging the interior walls of the column. Preferably, both the column and the retaining ring are formed of polyolefin material.

2 Claims, 4 Drawing Figures

LOWER SEALING MEANS FOR CHROMATOGRAPHIC COLUMN

BACKGROUND OF THE INVENTION

1. Field of the Invention

This invention relates to chromatographic columns for use in fluid phase separation processes; more particularly to an improved lower sealing means for such columns.

2. Description of the Prior Art

Chromatographic columns have long been used in the laboratory analysis of fluids. One particular type of chromatographic column is a disposable column used for separating compounds such as drugs from aqueous samples such as blood, urine, etc. The separation is accomplished by contacting a stationary phase, preferably spread over a large surface area, with a mobile phase to selectively dissolve compounds into the mobile phase and leave other compounds behind dissolved in the stationary phase. In the case of drug separation from blood or urine, the stationary phase is aqueous and is spread out on an adsorbent material packed into the column and the mobile phase is an immiscible organic solvent introduced into the inlet of the column for percolation through the packing material.

Disposable columns of the type just described have a phase separation membrane positioned beneath the packing material to permit passage of the mobile phase through the outlet of the column but to prevent passage of the stationary phase therethrough. It is crucial to the successful operation of the separation process that the phase separation membrane be sealed at its edges; otherwise, the stationary phase material can bypass the membrane and contaminate the mobile phase removed from the column as intended. The absence of proper sealing of the phase separation membrane results in what is known in the art as a "leaker".

A variety of sealing means for use as the lower seal in disposable phase-separation columns have been proposed, some of greater complexity than others. Yet an important factor to the commercial success of such disposable columns seems to have been overlooked; namely, the speed at which such columns may be assembled during the manufacturing process. If an effective sealing means requires time consuming operations for the construction and proper positioning of the seal within the column, the overall cost of the column becomes prohibitive as a disposable item.

SUMMARY OF THE INVENTION

The present invention overcomes the problems associated with known disposable phase separation columns by providing a reliable sealing means for the phase separation membrane, yet one that can be easily constructed and speedily assembled.

The present invention provides an improved lower sealing means for a disposable chromatographic column which includes a generally cylindrical hollow column constructed of polyolefin material and open at its inlet and outlet ends, the column being of substantially uniform interior diameter throughout its length but terminating with a tapered portion at its outlet end; the disposable column also is adapted to receive an adsorbent matrix for use in a two-phase fluid separation process. The improved lower sealing means of the present invention comprises: a disc of phase separation paper having a diameter slightly less than the diameter of the column and transversely disposed within the column adjacent the point at which the tapered portion commences; and a retaining ring having a flat base portion with a central opening of lesser dimension than the paper disc and having a circumferential flange formed of polyolefin material for sealingly engaging the interior of the column, the ring being dimensioned to be inserted into the column from its inlet end, with the flange extending away from the outlet end of the column, for sealing contact with the paper disc at its periphery. Preferably, the column is formed of rigid polypropylene and the flange is formed of flexible polyethylene integrally with the ring.

These and other features and advantages of the present invention will become apparent from the following description taken in conjunction with the accompanying drawings which illustrate a preferred embodiment.

DESCRIPTION OF THE PREFERRED EMBODIMENTS

Figure 1:
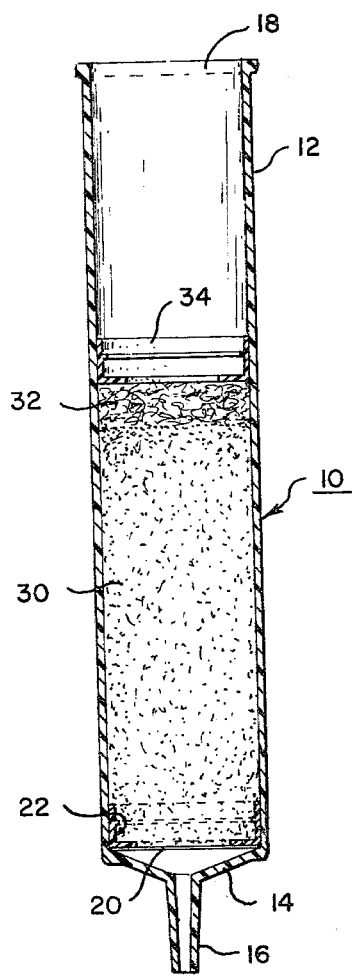
FIG. 1 is a longitudinal section of a chromatographic column embodying the present invention.

Referring to the drawings, there is shown a disposable chromatographic column 10 embodying the present invention. Column 10 includes a hollow tubular member or column 12 configured much the same as a conventional syringe housing used in hypodermic applications. Column 12 is of substantially uniform diameter throughout most of its length; in the lower portion, column 12 transitions abruptly but smoothly to a tapered, conical well portion 14 which terminates in a capillary outlet 16 at the bottom. Column 12 is open at its inlet end 18. Preferably, column 12 is molded from a polyolefin material such as polypropylene and is substantially rigid.

Figure 2:
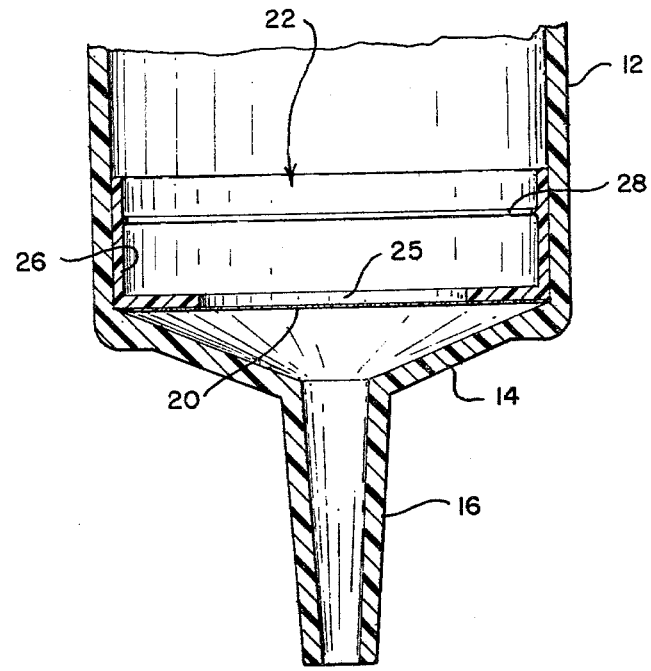
FIG. 2 is an enlarged sectional view of the lower portion of the column shown in FIG. 1.
Figure 3:
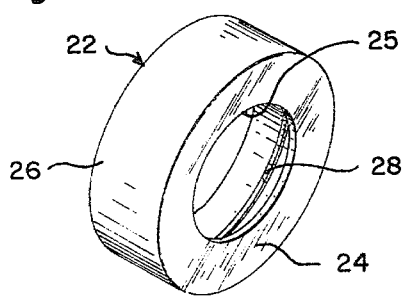
FIGS. 3 and 4 are perspective views in two different orientations of the retaining ring used in the present invention.
Figure 4:
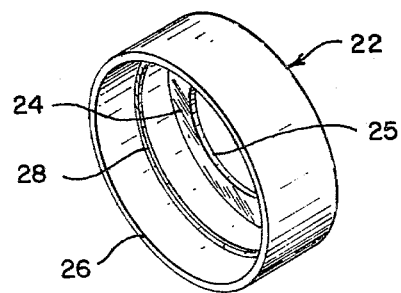

Disposed transversely of the longitudinal axis of column 12, immediately adjacent the point at which conical well portion 14 begins, is a thin disc of phase separation paper 20 (see FIG. 2). Paper disc 20 has a diameter slightly less than the uniform diameter of column 12 so that it may be dropped into column 12 through inlet 18 and will easily settle in the desired transverse orientation. Paper disc 20 is constructed of well-known fibrous material to be permeable to organic liquids but impermeable to aqueous liquids. Paper disc 20 has sufficient rigidity to minimize downward flexing when it is in position, even under the loading of an adsorbent matrix soon to be described.

Paper disc 20 is secured in position by retaining ring 22 which is forcibly inserted into column 12 through inlet 18 by use of an appropriate plug-like tool. Ring 22 has a flat, circular, outer base portion 24 and a circumferential flange 26 extending vertically from base 24. Flange 26 is formed of a polyolefin material, preferably integrally with base 24, and still further preferably of polyethylene to provide flexibility. Base 24 has a central opening 25 having a diameter less than the diameter of paper disc 20. When ring 22 is integrally molded, a mold release rib 28 is formed around the inner wall of flange 26.

The outside diameter of flange 26 is slightly larger than the uniform diameter of column 12 into which ring 26 is to be inserted. This tight frictional engagement with the interior wall of column 12, together with the electrostatic attraction normally exhibited by two polyolefinic materials (e.g. flange 26 and column 12), provides a tight seal between ring 22 and column 12, and thereby the passage of liquid between the interior wall of column 12 and flange 26 is prevented.

The second aspect of the sealing means of the present invention relates to contact between ring 22 and paper disc 20. As best seen in FIG. 2, the peripheral portion of base 24 of ring 22 actually contacts the periphery of paper disc 20 to pinch it against the uppermost inside circumference of conical well 14. This firm contact prevents any radially outward seepage of liquid between outer base portion 24 of ring 22 and the top surface of paper disc 20. Any such seepage, if permitted, would proceed to the edge of paper disc 20 and pass into conical well 14, bypassing the permeability properties of paper disc 20. Providing outer base portion 24 with a flat surface is deemed an important feature of this aspect of the present invention because any undulations, such as raised or depressed printing, on outer base portion 24 will tend to defeat the seal between ring 22 and paper disc 20.

It will be understood by those skilled in the art that the dimensions of ring 22 will vary with the diameter of column 12, not only in terms of the thickness of material of the ring but also in the height of flange 26 and, of course, its diameter. If the thickness of material is insufficient, ring 22 will tend to buckle upon insertion into column 12 and thus prolong insertion time and/or be unsatisfactory in performance. Further, if the height of flange 26 is too high, excessive friction between flange 26 and the interior walls of column 12 will result, thereby impairing or preventing smooth insertion of ring 22. On the other hand, a flange 26 that is too short will not form an effective seal with the interior walls of column 12. By way of example and not by way of limitation, the following dimensions are given: Column 12 has an inside diameter of 1.044 inches (2.65 cm). The outside diameter of flange 26 of ring 22 is 1.058 inches (2.68 cm). The height of flange 26 is 0.280 inches (0.71 cm). The material thickness of ring 22 is 0.035 inches (0.08 cm). The central opening 25 of ring 22 is 0.61 inches (1.54 cm). The diameter of paper disc 20 is 0.945 to 1.024 inches (2.4 to 2.6 cm).

Overlying retaining ring 22 and paper disc 20 in column 12 is packing material 30. Packing material 30 is present to provide a large surface area for adsorption of the stationary phase used in the particular process to which chromatographic column 10 is suited. Packing material 12 may be any one of a variety of well-known materials including diatomaceous earth, silica gel, cellulose, etc. Packing material 30 is retained in column 10 by a cotton or gauze stuffing 32 which is held down firmly by a second retaining ring 34. Retaining ring 34 is identical in construction to retaining ring 22.

What is claimed is:

1. In a disposable chromatographic column, including a generally cylindrical hollow column constructed of polyolefin material and being open at its inlet and outlet ends, said column having a substantially uniform interior diameter throughout its length but terminating with a tapered portion at its outlet end, said chromatographic column being adapted to receive an adsorbent matrix for use in a two-phase fluid separation process, an improved lower sealing means comprising:
   a disc of phase separation paper having a diameter slightly less than the diameter of said column and transversely disposed within said column adjacent the point at which said tapered portion commences; and
   a retaining ring having a flat base portion with a central opening of lesser dimension than said paper disc and having a circumferential flange formed of polyolefin material for sealingly engaging the interior of said column, said ring being dimensioned to be inserted into said column from said inlet end, with said flange extending away from outlet end of said column, for sealing contact with said paper disc at its periphery.

2. The improvement recited in claim 1 wherein:
said column is formed of rigid polypropylene and said flange is formed of flexible polyethylene integrally with said ring.

* * * * *